(12) United States Patent
Shainwald

(10) Patent No.: US 11,766,164 B2
(45) Date of Patent: Sep. 26, 2023

(54) ENDOSCOPE HANDPIECE

(71) Applicant: Medos International Sarl, Le Locle (CH)

(72) Inventor: Mark Shainwald, Raynham, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 17/806,561

(22) Filed: Jun. 13, 2022

(65) Prior Publication Data

US 2022/0304551 A1  Sep. 29, 2022

Related U.S. Application Data

(63) Continuation of application No. 16/595,931, filed on Oct. 8, 2019, now Pat. No. 11,382,489.

(51) Int. Cl.
*A61B 1/00* (2006.01)

(52) U.S. Cl.
CPC ...... *A61B 1/00105* (2013.01); *A61B 1/00042* (2022.02); *A61B 1/00066* (2013.01); *A61B 1/00117* (2013.01); *A61B 1/00181* (2013.01); *A61B 1/00183* (2013.01)

(58) Field of Classification Search
CPC .............. A61B 1/0008; A61B 1/00066; A61B 1/00105; A61B 1/00117; A61B 1/00181; A61B 1/00183
See application file for complete search history.

(56) References Cited

U.S. PATENT DOCUMENTS

| 4,919,112 A | 4/1990 | Siegmund |
| 5,621,830 A * | 4/1997 | Lucey ............... A61B 1/317 600/137 |
| 6,004,263 A | 12/1999 | Nakaichi et al. |
| 2012/0078050 A1 | 3/2012 | Schwartz et al. |
| 2014/0111634 A1 | 4/2014 | Mueckl et al. |
| 2021/0100431 A1 | 4/2021 | Shainwald |

FOREIGN PATENT DOCUMENTS

| CN | 114554929 A | 5/2022 |
| WO | WO 2009062202 A1 | 5/2009 |

* cited by examiner

*Primary Examiner* — Aaron B Fairchild
(74) *Attorney, Agent, or Firm* — Terrence J. Edwards; TechLaw Ventures, PLLC

(57) ABSTRACT

An endoscope handpiece and system may include an angle of view selector, a depressible button, which may be connected to a lock disposed within a port of the endoscopic handpiece. The system may further provide an endoscope, which may be connected to the handpiece via the port and locked in place by the lock.

19 Claims, 5 Drawing Sheets

ENDOSCOPE HANDPIECE

CROSS-REFERENCE TO RELATED APPLICATIONS

This application is a continuation of co-pending U.S. patent application Ser. No. 16/595,931 filed Oct. 8, 2019, entitled "Endoscope Handpiece," which is incorporated herein by reference in its entirety, including but not limited to those portions that specifically appear hereinafter, the incorporation by reference being made with the following exception: In the event that any portion of the above-referenced application is inconsistent with this application, this application supercedes said portion of said above-referenced application.

TECHNICAL FIELD

This disclosure relates generally to a handpiece for an endoscope used to assist a surgeon during surgical procedures.

STATEMENT REGARDING FEDERALLY SPONSORED RESEARCH OR DEVELOPMENT

Not Applicable.

BACKGROUND

Endoscopic surgery is experiencing rapid growth in the medical field. Endoscopy is a minimally invasive surgical procedure that is used to analyze the interior of a body cavity or interior surfaces of an organ by inserting a tubular member into the body cavity through a minor or minimal incision. A conventional endoscope is generally an instrument with a light source and an image sensor or device for visualizing the interior a body cavity. A wide range of applications have been developed for the general field of endoscopes including, but not necessarily limited to: arthroscope, angioscope, bronchoscope, choledochoscope, colonoscope, cytoscope, duodenoscope, enteroscope, esophago-gastro-duodenoscope (gastroscope), laparoscope, laryngoscope, nasopharyngo-neproscope, sigmoidoscope, thoracoscope, and utererscope (hereinafter referred to generally as "endoscope" or "scope"). The advantages of endoscopy include smaller surgical incisions and less soft tissue damage. As a result, there is significantly less discomfort and pain for a patient as well as a decrease in recovery time.

The advantages of minimally invasive surgery performed with the help of an endoscope are well known and understood in the medical field. As a result, there have been a growing number of devices for use with endoscopes for delivering, for example, diagnostic, monitoring, treatment, operating instruments, tools, and accessories (collectively, "tools") into the observation field and working space of the physician's endoscope.

Endoscopes typically are fashioned from several constituent elements. For example, an endoscope may include a handpiece, which connects to an endoscope element. The endoscope element may connect to a light source while the handpiece may further connect to a computing device having a processor (e.g., an image processing device) that receives and processes digital visual information obtained from the camera, which may be disposed, in at least many cases, in the handpiece or at a distal end of the scope, for example.

The handpiece of the endoscope is typically the point of interface between a surgeon and an endoscope. Accordingly, conventional handpieces have focused on ergonomic comfort for the surgeon to interface with the endoscope while also providing a handle to accurately and carefully manipulate the endoscope. Due to this focus on comfort and manipulation accuracy in conventional handpieces, many handpiece designs have not contemplated difficulties in design and assembly of the constituent parts of the endoscope. For example, conventional solutions for attaching an endoscope to an handpiece include using a threaded connection or couplers that frequently require two people to assemble (e.g., one person to hold the handpiece and another person to install the endoscope on the handpiece). Such conventional solutions are inconvenient and require additional surgical preparation time, which is undesirable.

Conventional endoscope cameras provide a particular field of view for a surgeon. In other words, the camera in the endoscope shows the surgeon a particular field of view for observing, for example, the inside of a body. Recent innovations in the art have provided new ways of observing different angles of view in a particular field of view. For example, these innovations allow for a surgeon to select a particular angle of view within a field of view based on an indication from the surgeon that a particular angle of view within a field of view is desirable. One such teaching is found within U.S. patent application Ser. No. 16/445,101, filed on Jun. 18, 2019 and entitled "Camera Scope Electronic Variable Prism" which, at least at the time of filing, is a co-owned application for patent with this application for patent. U.S. patent application Ser. No. 16/445,101, in one embodiment, teaches that different portions of an image sensor may be read out to provide different angles of view to a user. Accordingly, one object of this application is to provide an embodiment of an endoscopic handpiece that may be used in conjunction with the system of U.S. patent application Ser. No. 16/445,101 by disclosing a device for providing an angle of view selection input on a handpiece of an endoscope.

It is a further object of this disclosure to provide a handpiece of an endoscope that includes a button, which selectively locks an endoscope into the handpiece. It is yet another object of this application to provide an endoscope that that includes a plurality of user interface elements that allow for on-the-fly selection of a particular angle of view within a field of view of a camera for viewing on a remote display. It is yet a further object of this application to provide an endoscopic handpiece, which includes a button for selectively locking an endoscope into the handpiece and also provides user interface elements that allow for on-the-fly selection of a particular angle of view within a field of view of a camera for viewing on a remote display.

The features and advantages of the disclosure will be set forth in the description that follows, and in part will be apparent from the description, or may be learned by the practice of the disclosure without undue experimentation. The features and advantages of the disclosure may be realized and obtained by means of the instruments and combinations particularly pointed out herein.

SUMMARY OF THE DISCLOSURE

In one embodiment, an endoscope handpiece is disclosed. The endoscope handpiece may include an angle of view selector. The endoscope handpiece may further include a depressible button connected to a lock within a port of the endoscopic handpiece.

In another embodiment, a system is disclosed. The system may include an endoscopic handpiece and an endoscope. The endoscopic handpiece may include a depressible button connected to a lock within a port of the endoscopic handpiece.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
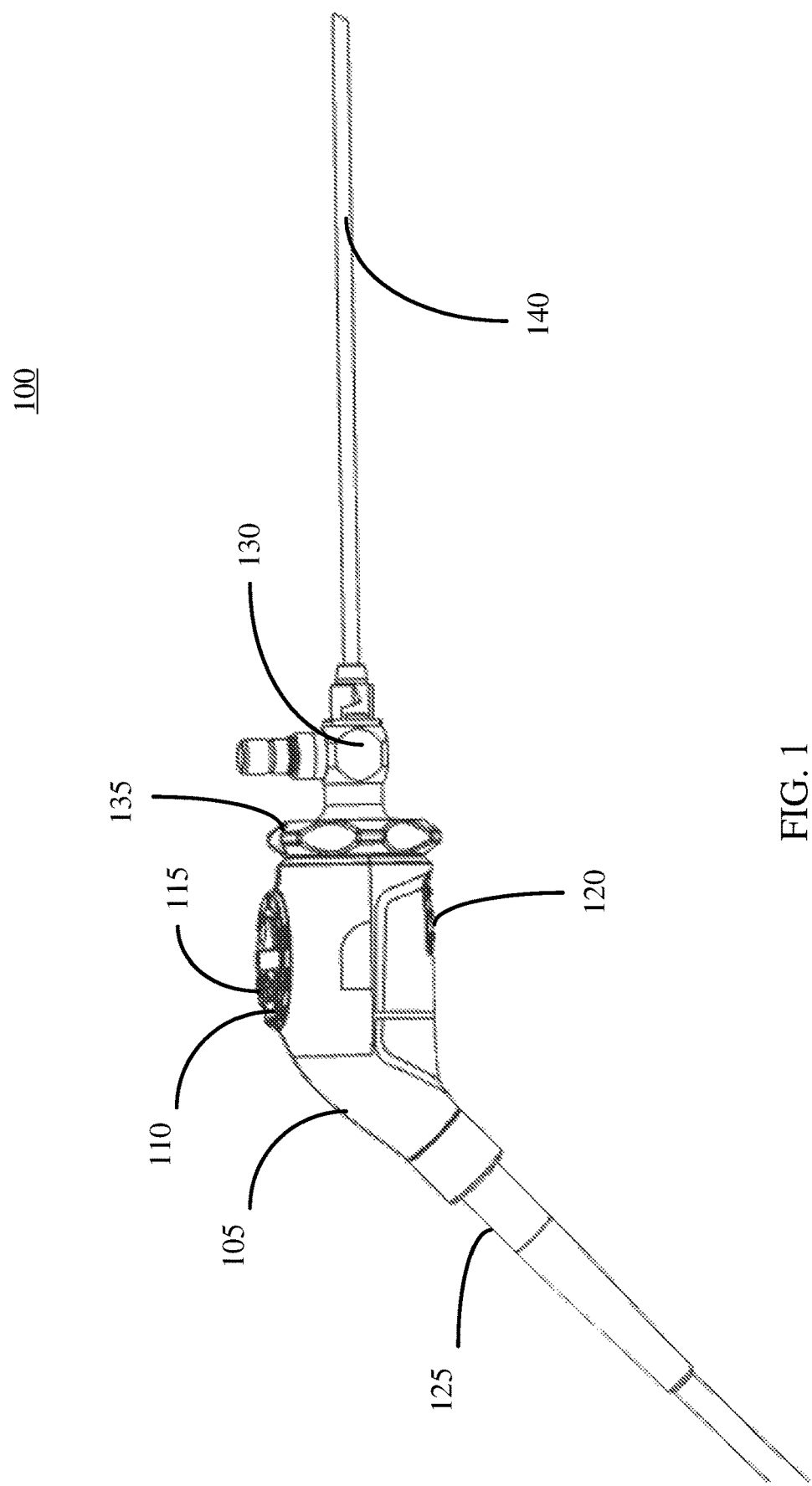
FIG. 1 illustrates side view of an exemplary endoscope system with a handpiece incorporating an endoscope install/release button and angle of view selector.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the devices, systems, methods and processes for providing a handpiece for an endoscope used to assist a surgeon during surgical procedures and an image or view optimizing assembly are disclosed and described, it is to be understood that this disclosure is not limited to the particular embodiments, configurations, or process steps disclosed herein as such embodiments, configurations, or process steps may vary somewhat. It is also to be understood that the terminology employed herein is used for the purpose of describing particular embodiments only and is not intended to be limiting since the scope of the disclosure will be limited only by the appended claims, if any, and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

It must be understood that "field of view" as used herein is intended to contemplate how much of an image can be seen in terms of degrees or angles as diffracted in liquids.

It must be understood that "angle of view" as used herein is intended to contemplate an angle at which a field of view is angled in degrees or angles as diffracted in liquids.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "active" as used in relation to a device or to electronic communication refers to any device or circuit, driven by hardware or software, that has decision making or logic processing capabilities regarding its operation and/or its condition. Conversely, the term "passive" as used in relation to an imaging device or to electronic communication refers to a hardware device that is written to and read from only, or a device that does not have any memory or other electronic, or physical tracking components and does not include any decision making or logic processing capabilities regarding its operation and/or its condition.

Referring now to the drawings, and specifically to FIG. 1, an embodiment of the features of the disclosure will be discussed generally. FIG. 1 illustrates a side view of an exemplary endoscope system 100 with a handpiece 105 incorporating an endoscope install/release button 120 and an angle of view selector 110. Handpiece 105 may include both an angle of view selector 110 and an endoscope install/release button 120 or may include one or the other of angle of view selector 110 and endoscope install/release button 120.

As shown in FIG. 1, angle of view selector 110 may be implemented as a dial with tactile indicators, which will be discussed below. Angle of view selector 110 may be positioned on a topmost portion of the handpiece 105, although other implementations are possible such as on either side of handpiece 105 to facilitate left or right handed surgeons. Angle of view selector 110 may further include user interface elements 115, which may also facilitate a change of angle of view for a camera (not shown) or may provide user control over other functions of endoscope system 100 (e.g., turning a light source on and off, turning the device on and off, etc.). User interface elements 115 may be implemented as buttons, levers, or any other device for supplying user input into a handpiece known in the art.

Handpiece 105 may further include a depressible button 120, which may be connected to a lock, discussed in more detail below, that allows the endoscope 130 to be selectively attached to the handpiece 105 and selectively removed from the handpiece 105 by simple depression of button 120. The function of the lock and button 120 will be discussed in more detail below.

Handpiece 105 may further include a wire connector 125 that connects the handpiece 105 to the endoscope system 100, which may receive information through endoscope 130 or that may be generated within handpiece 105 and which may also update and change a view of a scene within the field of view of a camera (not shown). Endoscope system 100 may further include an endoscope rotation element 135, which allows the endoscope to be rotated about an axis defined by an endoscope tube 140. The endoscope tube 140 may be selectively inserted into a body of a patient for performing surgical, inspection, or other operations and inspections.

Figure 2:
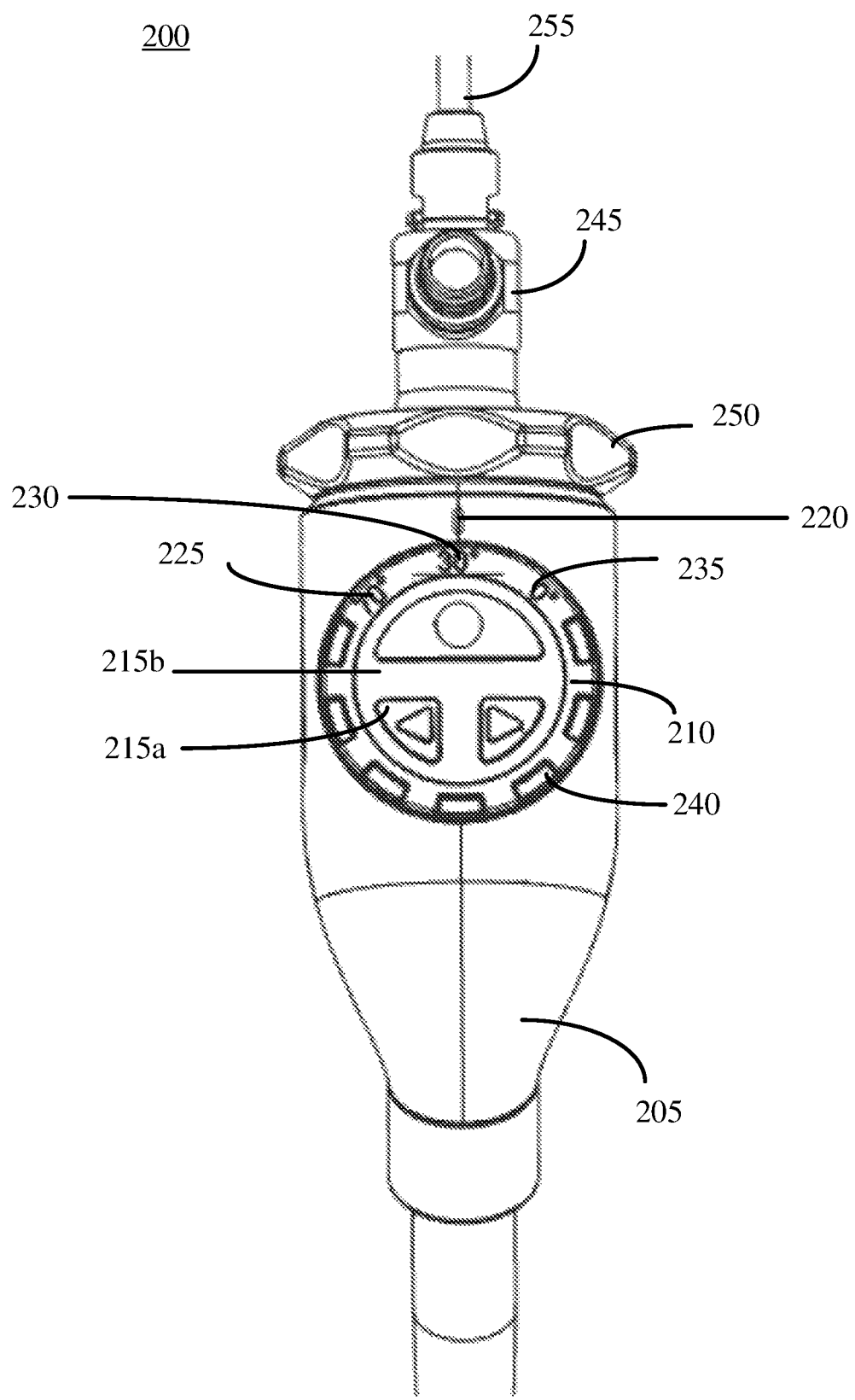
FIG. 2 illustrates a top view of an exemplary endoscopic unit with a handpiece incorporating an angle of view selector.

FIG. 2 illustrates a top view of an exemplary endoscopic unit 200 with a handpiece 205 incorporating an angle of view selector 210. The angle of view selector 210 may be implemented as a dial, as shown in FIG. 2, or may also be implemented as one or more interface elements 215a, as shown in FIG. 2. As shown in FIG. 2, the angle of view selector 210 is implemented as a dial, which may be selectively rotated to adjust an angle of view shown on a display based on the field of view of a scene as viewed through endoscope 245. In one embodiment, angle of view selector 210 may be implemented to provide three discrete and selectable angles of view, such as 0° (see reference numeral 235), 30° (see reference numeral 230), and 70° (see reference numeral 225). A user may interact with the angle of view selector 210 to align a selected angle of view with an indicator 220 positioned on the handpiece 205 in order to instruct an endoscope system to provide a view of the selected angle of view.

As shown in FIG. 2 and by way of example, a dial is implemented as angle of view selector 210 and has been rotated such that a 30° angle of view is aligned with indicator 220. In this exemplary case, an electrical signal may be generated by a sensor (not shown) associated with angle of view selector 210 (not shown), which indicates to an endoscope system that the user has selected a 30° angle of view for the field of view provided by the camera (not shown). Angle of view selector 210 may also include tactile elements 240, which assist a surgeon in turning the dial, increase grip friction, allow the surgeon to turn the dial with a single finger or a thumb, or otherwise facilitate the turning of the dial. In addition, or alternatively, audio and tactile feedback may be provided by handpiece 205 that indicates an angle of view that has been selected by the user without the user having to specifically look at indicator 220 or angle of view selector 210.

As noted above, angle of view selector 210 may also be implemented with user interface elements, such as one or more user interface elements 215a. An insert 215b may be used to cover one or more user interface elements 215a in a manner that allows endoscopic unit 200 to remain sealed while the one or more user interface elements 215a are exposed for receiving user input. In this embodiment, user interface elements 215a may allow a user to change a selected angle of view independent of angle of view selector 210. In this manner a user may press a directional element of one or more interface elements 215a or an opposite directional element which allows a user to scroll, in a continuous manner, between different angles of view in a field of view. For example, a user may scroll an angle of view of a field of view from 0° to 70° in an incremental manner (e.g., by 1° increments or half degree increments, by 2-5 degree increments, by 10 degree increments and etc.). It is possible that a user may also automatically flip between a 0° view, a 30° view, and a 70° view with a simple press of a one or more of user interface elements 215a as well (or in reverse with a push of another of the one or more of user interface elements 215a).

As previously discussed, endoscopic unit 200 may include an endoscope 245 that includes a rotation element 250 and an endoscope tube 255. Endoscope 245 may connect to handpiece 205 using the techniques, devices, and/or systems described herein.

Figure 3:
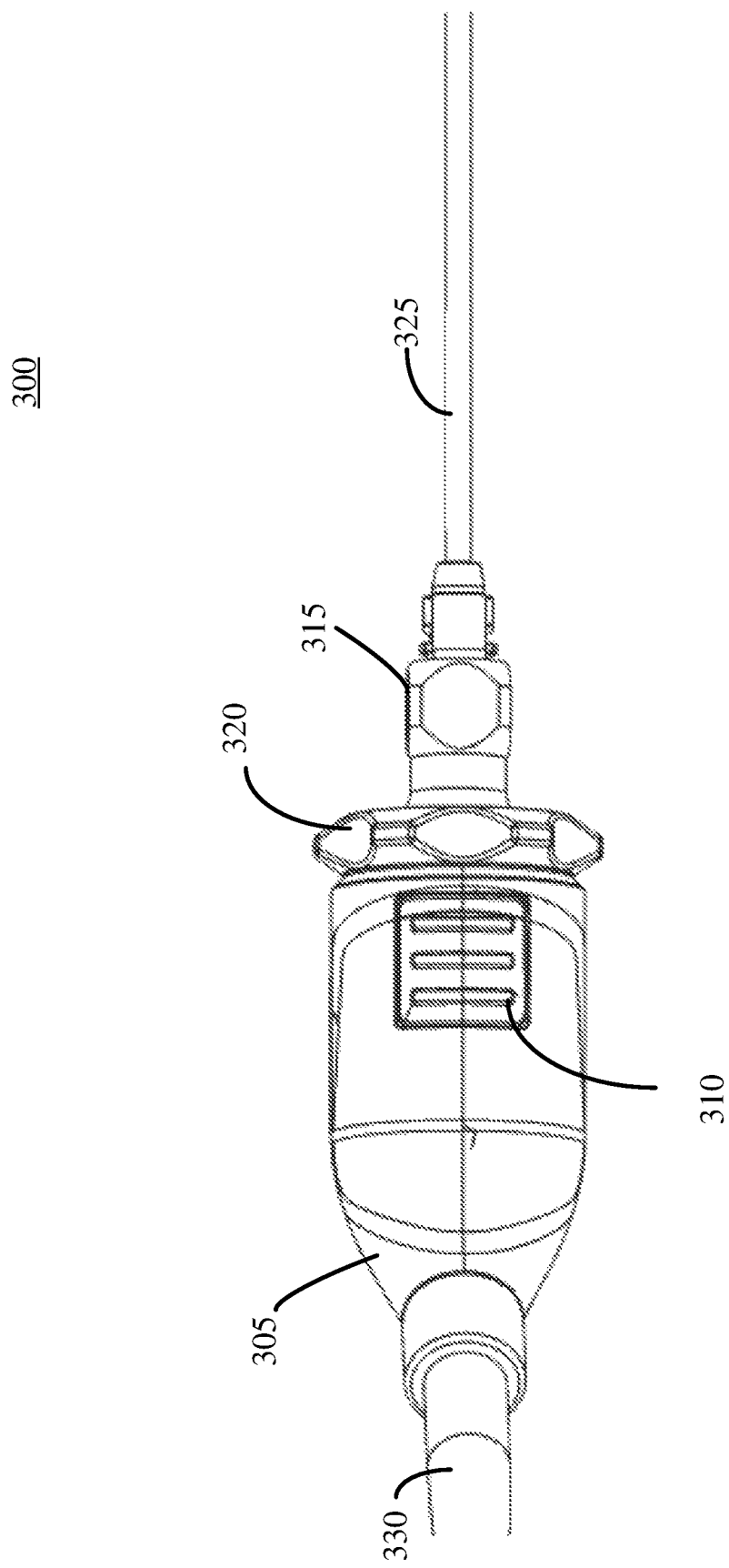
FIG. 3 illustrates a bottom view of an exemplary endoscopic unit with a handpiece incorporating an endoscope install/release button.

FIG. 3 illustrates a bottom view of the exemplary endoscopic unit 300 with a handpiece 305 incorporating an endoscope install/release button 310. Endoscope install/release button 310 may be a depressible button, which may be depressed in response to a user pushing on endoscope install/release button 310. When the endoscope install/release button 310 is depressed, the endoscope 315 becomes unlocked from the handpiece 305 and may be removed by a user simply by pulling the endoscope 315 from the handpiece 305. The endoscope 315 may include an endoscope rotation element 320 and an endoscope tube 325. The handpiece 305 may further be connected by a connection 330 to an endoscopic system that processes visual data received from the camera (not shown) through the endoscope 315 and the user interface commands (e.g., a turn of a dial or a press of a button, etc.) provided via the handpiece 305.

Figure 4:
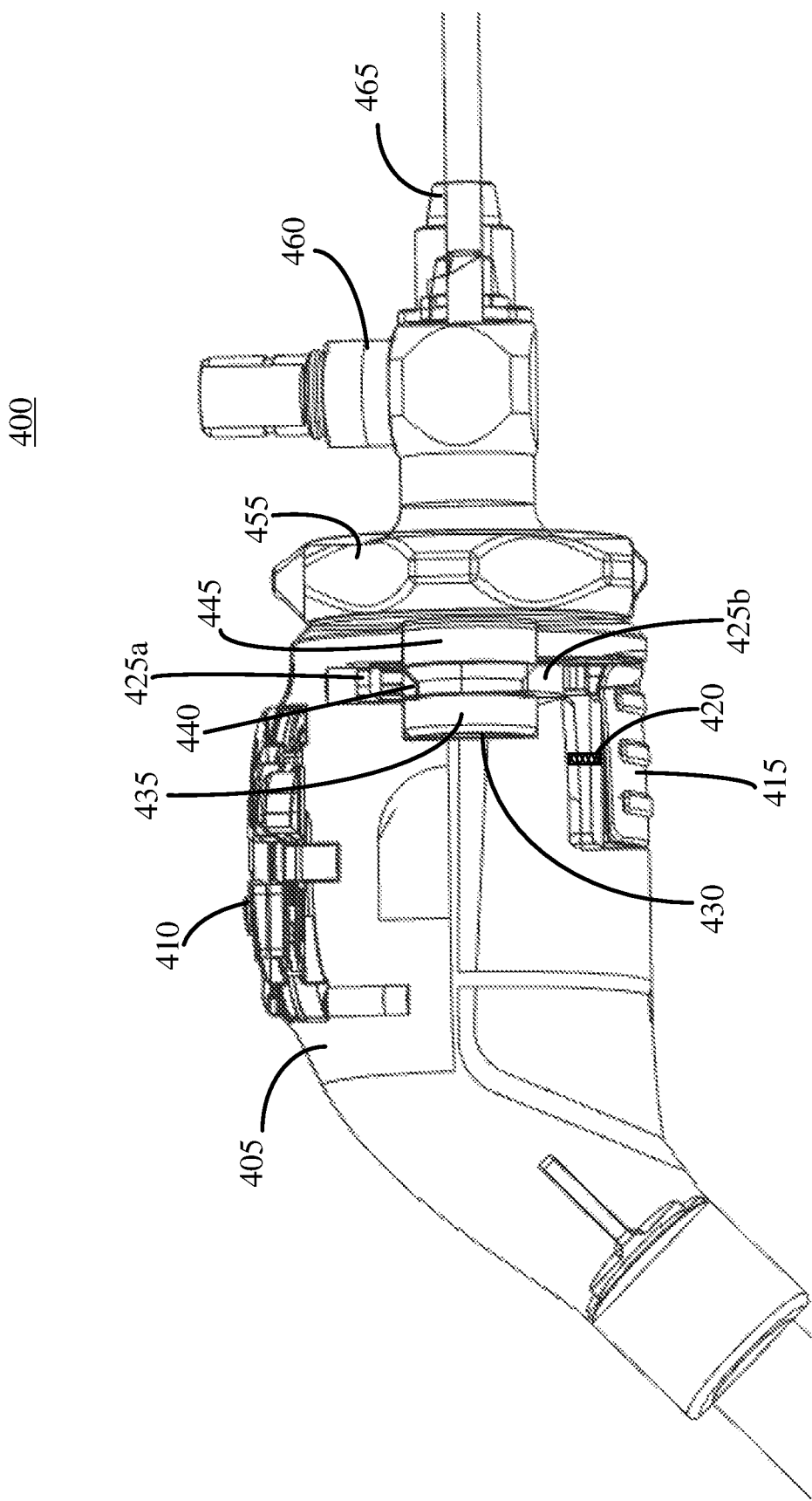
FIG. 4 illustrates a horizontal cross section of an exemplary endoscopic unit handpiece with connected endoscope.

FIG. 4 illustrates a horizontal cross section of an exemplary endoscopic unit 400 with a handpiece 405 connected to an endoscope element 460. The endoscopic unit 400 is shown in FIG. 4 with the handpiece 405 as a discrete unit, although the handpiece 405 may be connected to an endoscope system. As shown in FIG. 4, the endoscopic unit 400 also includes a dial 410, which receives interaction from a user and, in response, causes the endoscope system to alter an angle of view of a field of view of a camera (not shown).

The endoscopic unit 400 further includes a depressible endoscope install/release button 415, which selectively allows the endoscope 460 to be installed in and removed from the handpiece 405, as discussed below. The handpiece 405 includes a spring element 420, which may be connected to the endoscope install/release button 415 and allows the button 415 to be selectively depressed in response to a user pressing on the endoscope install/release button 415. The spring element 420 may be biased to cause the endoscope install/release button 415 to be disposed in and remain in an undepressed condition when pressure is not applied to the endoscope install/release button 415 by a user's hand or finger. When the endoscope install/release button 415 is depressed, the spring 420 compresses and pushes a chamfered dog 425a towards a top of the handpiece 405 and allows a corresponding spacer 425b to fully open a port 430 to receive an endoscope connector 435. The endoscope connector 435 may be disposed within port 430 when the endoscope install/release button 415 is depressed (or in some embodiments may be installed simply by pushing the endoscope connector 435 into port 430 and relying on chamfered dog 425a to be pushed out of port 430 by endoscope connector 435). When the endoscope install/release button 415 returns to an undepressed condition, the chamfered dog 425a slides into a mating chamfered channel 440 disposed between an endoscope spacer 445 and the endoscope connector 435. The chamfered dog 425a may include a portion that is angled to match a corresponding angle of the chamfer in chamfered channel 440 of endoscope 460. The chamfered dog 425a may also include a squared or right angle portion, which mates with a frontmost side of the endoscope connector 435 (e.g., a side of the chamfered channel 440 that is opposite the side of chamfered channel 440 that is angled to mate with chamfered dog 425a). In this manner, the chamfered dog 425a secures the endoscope 460 to the handpiece 405 by maintaining contact between the endoscope connector 435 and the handpiece 405 within the port 430 by applying pressure to the endoscope connector 435, which rigidly retains the endoscope 460 within the port 430.

The endoscope 460 may include a rotation element 455 and an endoscope tube 465, which allows the endoscope 460 to rotate around a horizontal axis defined by the endoscope tube 465.

Figure 5:
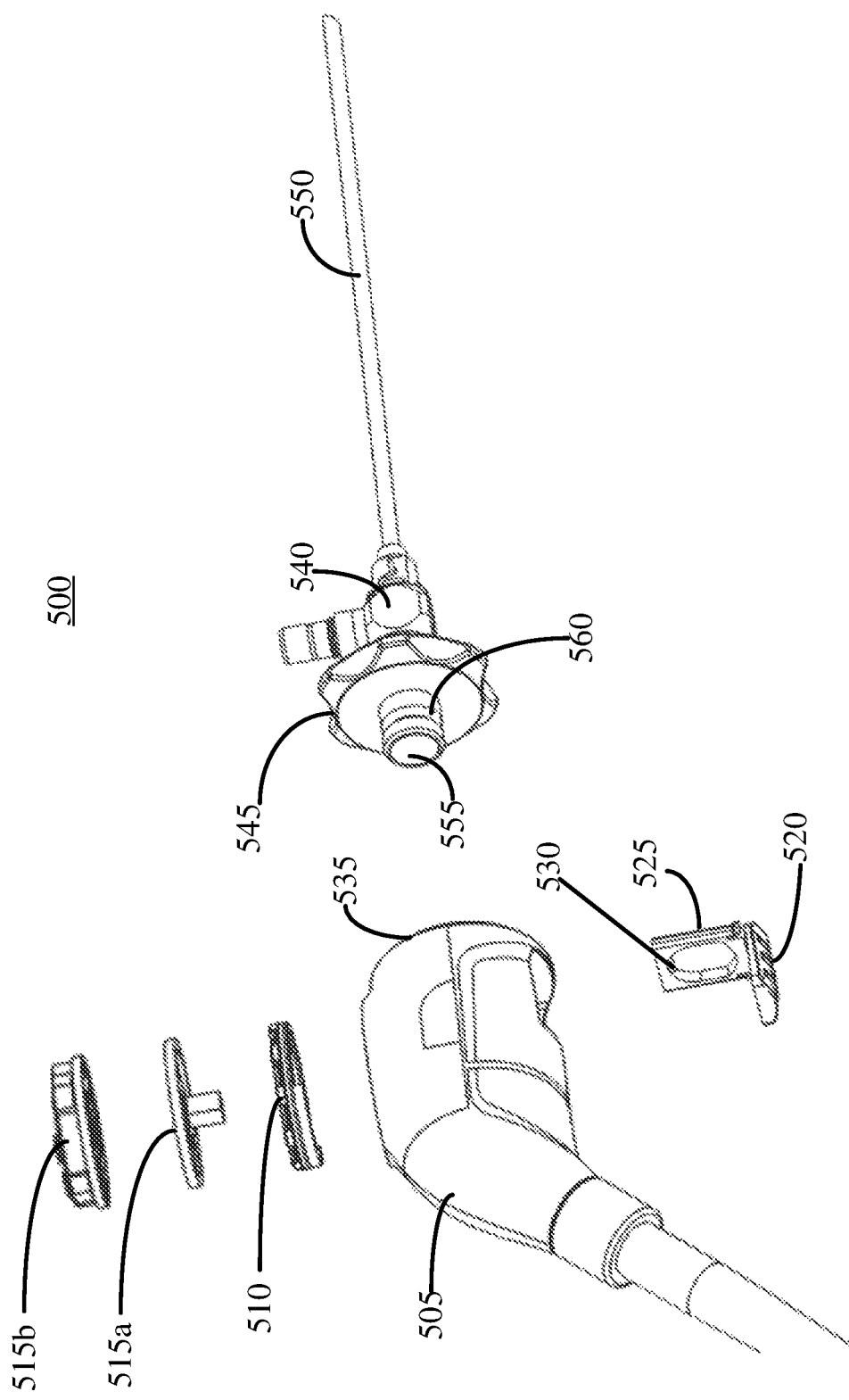
FIG. 5 illustrates an exploded view of at least some constituent components of an exemplary endoscopic unit with a handpiece incorporating an endoscope install/release button and an angle of view selector.

FIG. 5 illustrates an exploded view of at least some constituent components of an exemplary endoscope 500 with a handpiece 505 incorporating an endoscope install/release button 520 and an angle of view selector 510. Endoscope 500 may include an angle of view selector 510, one or more user interface elements 515a and an insert 515b. The handpiece 505, angle of view selector 510, and one or more user interface elements 515a, and insert 515b may be similar in implementation and description to similar elements described above with respect to FIG. 2. As described herein, the angle of view selector 510 may be a dial or implemented as one or more user interface elements 515a to cause an endoscopic system to change an angle of view in a field of view based on user input. In this manner, a user may interact with an angle of view selector 510 or one or more user interface elements 515a to adjust the angle of view or field of view according to the user's preferences. The angle of view selector 510 may trigger a mechanical or electrical sensor, which causes a signal to be transmitted to an endoscope system that indicates to the endoscope system that a particular angle of view in the field of view has been selected by the user.

The handpiece 505 may further include a button 520 having a lock 525 and a chamfered dog 530, which allow an endoscope 540 to be inserted into a port 535 of the handpiece 505 and retained therein, according to the foregoing disclosure. Endoscope 540 may include an endoscope rotation element 545 and an endoscope tube 550. Endoscope 540 may further include an endoscope connector 555, which includes a chamfered channel 560. The chamfered channel 560 may interface with the chamfered dog 530 to secure the endoscope 540 within the port 535 of the handpiece 505 according to the foregoing description.

In this manner, a simple connection is provided between the endoscope 540 and the handpiece 505. A user may simply push the endoscope 540 into the port 535 and as the endoscope connector 555 contacts the chamfered dog 530, the endoscope connector 555 will overcome spring pressure exerted by a spring element (not shown in FIG. 5) to push the chamfered dog 530 out of the path of the endoscope connector 555 in the port 535 and allow the endoscope connector 555 to fully seat within the port 535 of the handpiece 505. Alternatively, the user may apply pressure to the endoscope install/release button 520 while inserting the endoscope connector 555 into the port 535 to a point where the endoscope connector 555 passes the chamfered dog 530 and thereafter releases pressure to the endoscope install/release button 520. In either case, the chamfered dog 530 may, by pressure exerted by the spring element (not shown in FIG. 5), rest within the chamfered channel 530 and secure the endoscope 540 to the handpiece 505 according to the foregoing description. To remove the endoscope 540, the endoscope install release button 520 may be depressed by a user to disengage the chamfered dog 530 from the chamfered channel 560 and allow the endoscope 540 to be removed from the handpiece 505 through the port 535.

EXAMPLES

The following examples pertain to features of further embodiments of the disclosure:

In Example 1 of the disclosure, an endoscope handpiece may include an angle of view selector, and a depressible button connected to a lock within a port of the endoscopic handpiece.

Example 2 of the disclosure includes the endoscope handpiece of Example 1, wherein the angle of view selector is a dial.

Example 3 of the disclosure includes the endoscope handpiece of any of Examples 1-2, wherein the dial triggers an electronic sensor to select an angle of view to be displayed.

Example 4 of the disclosure includes the endoscope handpiece of any of Examples 1-3, wherein the angle of view selected by the dial is 0°, or is 30°, or is 70°.

Example 5 of the disclosure includes the endoscope handpiece of any of Examples 1-4, wherein the lock includes a chamfered dog.

Example 6 of the disclosure includes the endoscope handpiece of any of Examples 1-5, wherein the chamfered dog includes an angled portion.

Example 7 of the disclosure includes the endoscope handpiece of any of Examples 1-6, wherein the chamfered dog includes a square portion.

Example 8 of the disclosure includes the endoscope handpiece of any of Examples 1-7, wherein the lock includes a spacer disposed opposite of a chamfered dog installed on the lock.

Example 9 of the disclosure includes the endoscope handpiece of any of Examples 1-8, further comprising: one or more user interface elements.

Example 10 of the disclosure includes the endoscope handpiece of any of Examples 1-9, further comprising a connector connecting the endoscopic handpiece to an image processing device.

In Example 11 of the disclosure, a system includes an endoscope handpiece that comprises an angle of view selector, and a depressible button connected to a lock within a port of the endoscopic handpiece; and the system further includes an endoscope.

Example 12 of the disclosure includes the system of Example 11, wherein the angle of view selector is a dial.

Example 13 of the disclosure includes the system of any of Examples 11-12, wherein the angle of view selected by the dial is one of 0°, 30°, and 70°.

Example 14 of the disclosure includes the system of any of Examples 11-13, wherein the lock includes a chamfered dog.

Example 15 of the disclosure includes the system of any of Examples 11-14, wherein the chamfered dog includes an angled portion which corresponds to a chamfer in a chamfered channel on the endoscope.

Example 16 of the disclosure includes the system of any of Examples 11-15, wherein the chamfered dog includes a square portion which interfaces with an endoscope connector on the endoscope.

Example 17 of the disclosure includes the system of any of Examples 11-16, wherein the lock includes a chamfered dog which connects to a chamfered channel in the endoscope.

Example 18 of the disclosure includes the system of any of Examples 11-17, wherein the endoscope connects to the handpiece via the port.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications and their equivalents.

What is claimed is:

1. A device comprising:
   an endoscope handpiece comprising:
   an angle of view selector comprising a dial in electronic communication with an electronic sensor configured to adjust an angle of view shown on a display, and
   a depressible button connected to a lock within a port of the endoscopic handpiece;
   an endoscope tube; and
   an endoscope rotation element comprising a grip and an endoscope connector, wherein the grip is configured to rotate the endoscope tube relative to the endoscope handpiece;
   wherein the lock of the depressible button joins the endoscope tube to the endoscope handpiece by securing the endoscope connector within the port of the endoscopic handpiece.

2. The device of claim 1, wherein the angle of view selector further comprises one or more interface elements.

3. The device of claim 1, wherein the dial comprises one or more selectable angles of view and the dial is configured to align a user-selected angle of view with an indicator on the endoscope handpiece to trigger the electronic sensor to select the angle of view corresponding to the user-selected angle of view to be displayed.

4. The device of claim 3, wherein one of the one or more selectable angles of view on the dial is 0°.

5. The device of claim 3, wherein one of the one or more selectable angles of view on the dial is 30°.

6. The device of claim 3, wherein one of the one or more selectable angles of view on the dial is 70°.

7. The device of claim 1, wherein the lock includes a chamfered dog.

8. The device of claim 7, wherein the chamfered dog includes an angled portion.

9. The device of claim 7, wherein
   the lock comprises a chamfered channel to matingly receive the chamfered dog therein;
   wherein the chamfered dog includes a right angle portion that is configured to matingly engage the endoscope connector.

10. The device of claim 1, wherein the lock includes a spacer disposed opposite of a chamfered dog installed on the lock.

11. The device of claim 1, further comprising: one or more user interface elements.

12. The device of claim 1, further comprising a connector configured to connect the endoscopic handpiece to an image processing device.

13. An endoscopic device, comprising:
    an endoscope handpiece comprising:
    an angle of view selector comprising one or more interface elements in electronic communication with an electronic sensor configured to adjust an angle of view shown on a display, and
    a depressible button connected to a lock within a port of the endoscopic handpiece,
    wherein the endoscope handpiece is configured to provide audio or tactile feedback when the angle of view is selected;
    an endoscope tube; and
    an endoscope rotation element comprising a handle and an endoscope connector, wherein the handle is configured to rotate the endoscope tube relative to the endoscope handpiece;
    wherein the lock of the depressible button joins the endoscope tube to the endoscope handpiece by securing the endoscope connector within the port of the endoscopic handpiece.

14. The device of claim 13, wherein the one or more interface elements comprises:
    one or more of a button or a lever, and
    one or more selectable angles of view.

15. The device of claim 14, wherein a selected angle of view selected from the one or more selectable angles of view is one of 0°, 30°, and 70°.

16. The device of claim 13, wherein the lock includes a chamfered dog.

17. The device of claim 16, wherein the chamfered dog includes an angled portion which corresponds to a chamfer in a chamfered channel on the endoscope connector.

18. The device of claim 17, wherein the chamfered dog includes a right angle portion which interfaces with the endoscope connector.

19. The device of claim 13, wherein the lock includes a chamfered dog which connects to a chamfered channel in the endoscope connector.

* * * * *